US009856515B2

(12) United States Patent
Bruinsma et al.

(10) Patent No.: US 9,856,515 B2
(45) Date of Patent: *Jan. 2, 2018

(54) REMOVAL OF PCR INHIBITORS

(71) Applicant: Exact Sciences Corporation, Madison, WI (US)

(72) Inventors: Janelle J. Bruinsma, Madison, WI (US); Hemanth D. Shenoi, Verona, WI (US); Michael J. Domanico, Middleton, WI (US); James P. Light, II, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 152 days.

This patent is subject to a terminal disclaimer.

(21) Appl. No.: 14/636,366

(22) Filed: Mar. 3, 2015

(65) Prior Publication Data

US 2015/0176063 A1 Jun. 25, 2015

Related U.S. Application Data

(63) Continuation of application No. 13/469,989, filed on May 11, 2012, now Pat. No. 8,993,341.

(60) Provisional application No. 61/485,338, filed on May 12, 2011.

(51) Int. Cl.
*C12Q 1/68* (2006.01)
*C12N 15/10* (2006.01)

(52) U.S. Cl.
CPC ....... *C12Q 1/6806* (2013.01); *C12N 15/1003* (2013.01); *C12N 15/1006* (2013.01); *C12N 15/1017* (2013.01); *Y10T 436/25125* (2015.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. |
| 4,683,058 A | 7/1987 | Lyman et al. |
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,647,990 A | 7/1997 | Vassarotti |
| 5,648,212 A | 7/1997 | Albertsen et al. |
| 5,660,988 A | 8/1997 | Duck et al. |
| 5,710,264 A | 1/1998 | Urdea et al. |
| 5,773,258 A | 6/1998 | Birch et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,133,436 A | 10/2000 | Koster et al. |
| 6,150,097 A | 11/2000 | Tyagi et al. |
| 6,183,960 B1 | 2/2001 | Lizardi |
| 6,210,884 B1 | 4/2001 | Lizardi |

(Continued)

FOREIGN PATENT DOCUMENTS

| | | |
|---|---|---|
| CN | 100368566 | 2/2008 |
| CN | 101307311 | 11/2008 |

(Continued)

OTHER PUBLICATIONS

Ashland (Polyplasdone crospovidone superdisintegrants, attached, accessed Jul. 26, 2016).*
Sigma (Poly(vinylpolypyrrolidone) Product Sheet, attached, Dec. 2002).*
MadSci Network (Re: PCR inhibitors—how to get rid of them?, post by Shireef Darwish, attached, Nov. 20, 2006).*
Nassuth et al. (Improved RNA extraction and one-tube RT-PCR assay for simultaneous detection of control plant RNA plus several viruses in plant extracts, J Virol Methods. Oct. 2000;90(1):37-49).*
Fotedar et al. (Laboratory Diagnostic Techniques for Entamoeba Species, Clinical Microbiology Reviews, Jul. 2007, p. 511-532).*

(Continued)

*Primary Examiner* — Aaron A Priest
(74) *Attorney, Agent, or Firm* — Casimir Jones, S.C.; Mary Ann D. Brow

(57) ABSTRACT

Provided herein is technology relating to processing and preparing samples and particularly, but not exclusively, to methods, systems, and kits for removing assay inhibitors, e.g., compounds that inhibit polymerase chain reaction, from samples comprising nucleic acids. In particular, the technology is directed toward treating crude sample preparations, such as supernatants from homogenized stool samples, with insoluble polyvinylpyrrolidone (PVP) to form PVP-assay inhibitor complexes, and filtration to separate the PVP-assay inhibitor complexes from the crude sample preparations to produce clarified samples that exhibit reduced assay inhibition.

8 Claims, 15 Drawing Sheets

(56) References Cited

U.S. PATENT DOCUMENTS

| | | | |
|---|---|---|---|
| 6,221,583 B1 | 4/2001 | Kayyem et al. | |
| 6,221,655 B1 | 4/2001 | Fung et al. | |
| 6,235,502 B1 | 5/2001 | Weissman et al. | |
| 6,248,229 B1 | 6/2001 | Meade | |
| 6,444,461 B1 | 9/2002 | Knapp et al. | |
| 6,872,816 B1 | 3/2005 | Hall et al. | |
| 6,992,182 B1* | 1/2006 | Muller | C12Q 1/6806 435/91.5 |
| 7,005,266 B2 | 2/2006 | Sprenger-Haussels | |
| 7,387,874 B2 | 6/2008 | Gocke et al. | |
| 7,662,594 B2 | 2/2010 | Kong et al. | |
| 7,931,920 B2 | 4/2011 | Hillebrand | |
| 8,530,228 B2 | 9/2013 | Han et al. | |
| 8,574,890 B2 | 11/2013 | Icenhour et al. | |
| 8,808,990 B2 | 8/2014 | Lidgard et al. | |
| 8,980,107 B2 | 3/2015 | Domanico et al. | |
| 8,993,341 B2 | 3/2015 | Bruinsma et al. | |
| 8,999,176 B2 | 4/2015 | Domanico et al. | |
| 9,000,146 B2 | 4/2015 | Bruinsma et al. | |
| 2001/0035375 A1 | 11/2001 | Humicke-Smith | |
| 2002/0164631 A1 | 11/2002 | Shuber et al. | |
| 2003/0013112 A1 | 1/2003 | Haussels | |
| 2003/0173284 A1* | 9/2003 | Baker | B01L 3/0275 210/321.6 |
| 2005/0026175 A1 | 3/2005 | Link et al. | |
| 2006/0172302 A1 | 8/2006 | Hermansen et al. | |
| 2006/0172331 A1 | 8/2006 | Sprenger-Haussels | |
| 2006/0270843 A1 | 11/2006 | Hall et al. | |
| 2007/0202525 A1 | 8/2007 | Quake et al. | |
| 2008/0299621 A1 | 12/2008 | Tatnell et al. | |
| 2009/0253142 A1 | 10/2009 | Allawi et al. | |
| 2010/0129828 A1 | 5/2010 | Beaulieu et al. | |
| 2010/0151456 A1 | 6/2010 | Ataman-Onal et al. | |
| 2011/0105346 A1 | 5/2011 | Beattie et al. | |
| 2012/0122088 A1 | 5/2012 | Zou et al. | |
| 2012/0122105 A1 | 5/2012 | Oldham-Haltom et al. | |
| 2012/0122106 A1 | 5/2012 | Zou et al. | |
| 2014/0193813 A1 | 7/2014 | Bruinsma et al. | |
| 2014/0194607 A1 | 7/2014 | Lidgard et al. | |
| 2014/0194608 A1 | 7/2014 | Lidgard et al. | |
| 2015/0010907 A1 | 1/2015 | Lidgard et al. | |
| 2015/0284770 A1 | 10/2015 | Bruinsma et al. | |
| 2016/0130635 A1 | 5/2016 | Bruinsma et al. | |

FOREIGN PATENT DOCUMENTS

| | | | |
|---|---|---|---|
| CN | 101680025 | 3/2010 | |
| CN | 101935647 | 7/2012 | |
| EP | 265244 | 4/1988 | |
| EP | 1371736 B1 * | 8/2006 | C12Q 1/701 |
| JP | 2010-533851 | 10/2010 | |
| JP | 2010-533853 | 10/2010 | |
| WO | WO 90/11345 | 10/1990 | |
| WO | WO 2004108925 | 12/2004 | |
| WO | WO 2005023091 | 3/2005 | |
| WO | WO 2008084219 | 7/2008 | |
| WO | WO 2008150826 | 12/2008 | |
| WO | WO 2010014970 | 2/2010 | |
| WO | WO 2010028382 | 3/2010 | |
| WO | WO 2010028382 A2 * | 3/2010 | A61B 10/0038 |
| WO | WO 2011014970 | 2/2011 | |
| WO | WO 2012002887 | 1/2012 | |
| WO | WO 2012155072 | 11/2012 | |

OTHER PUBLICATIONS

Morgan et al. (Comparison of PCR and Microscopy for Detection of Cryptosporidium parvum in Human Fecal Specimens: Clinical Trial, Journal of Clinical Microbiology, Apr. 1998, p. 995-998).*
Verweij et al. (Detection and Identification of Entamoeba Species in Stool Samples by a Reverse Line Hybridization Assay, Journal of Clinical Microbiology, Nov. 2003, p. 5041-5045).*
Chemical Book (Polyvinylpyrrolidone, attached, available at http://www.chemicalbook.com/chemicalproductproperty_en_cb4209342.htm, Aug. 3, 2010).*
Qiagen, QIAamp DNA Stool Mini Kit Handbook, Aug. 1, 2001 (Year: 2001).*
Trochimchuk et at, "A comparison of DNA extraction and purification methods to detect Escherichia coli O157:H7 in cattle manure," J Microbiol Methods, 2003, 54:165-175.
Ahlquist et al., "HemoQuant, a new quantitative assay for fecal hemoglobin. Comparison with Hemoccoult," Ann Intern Med, 1984, 101:297-302.
Ahlquist et al., "Colorectal Cancer Screening by Detection of Altered Human DNA in Stool: Feasibility of a Multitarget Assay Panel," Gastroenterology, 2000, 119: 1219-1227.
Andreadis and Chrisey, "Use of immobilized PCR primers to generate covalently immobilized DNAs for in vitro transcription/translation reactions," Nucleic Acids Res, 2000, 28:e5, 8 pages.
Aquamira Technologies, "Some Important Words in Regards to Filter Ratings," retrieved Oct. 3, 2014.
Ballabio, et al., "Screening for steroid sulfatase (STS) gene deletions by multiplex DNA amplification," Human Genetics, 1990, 84(6): 571-573.
Barnay, "Genetic disease detection and DNA amplification using cloned thermostable ligase," Proc. Natl. Acad. Sci USA, 1991, 88:189-93.
Beaucage et al., "Deoxynucleoside phosphoramidites—A new class of key intermediates for deoxypolynucleotide synthesis," Tetrahedron Lett., 1981, 22: 1859-1862.
Berthelet et al., "Rapid, direct extraction of DNA from soils for PCR analysis using polyvinylpolypyrrolidone spin columns," FEMS Microbiology Letters, 1996, 138:17-22.
Brown et al., "Chemical synthesis and cloning of a tyrosine tRNA gene," Meth Enzymol., 1979, 68:109-151.
Bustin, "Absolute quantification of mRNA using real-time reverse transcription polymerase chain reaction assays," J. Molecular Endocrinology, 2000, 25:169-193.
Chamberlain et al., "Deletion screening of the Duchenne muscular dystrophy locus via multiplex DNA amplification," Nucleic Acids Research, 1988, 16(23):11141-11156.
Cullen et al., "Simple and rapid method for direct extraction of microbial DNA from soil for PCR", Soil Biology and Biochemistry, vol. 30, No. 8/9, 1998, pp. 983-993.
Don et al., "'Touchdown' PCR to circumvent spurious priming during gene amplification," Nucleic Acids Research, 1991, 19(14):4008.
Doulton USA, "Absolute Vs. Nominal Microns Pore Ratings," Retrieved Oct. 3, 2014, from http;//doultonusa.com/HTML pages/absolute_vs_nominal_microns_rating.htm.
European Search Report dated Oct. 27, 2014, EP Patent Application No. 12782489.4, 9 pages.
Fotedar et al., "Laboratory Diagnostic Techniques for Entamoeba Species," Clinical Microbiology Reviews, 2007, 20(3):511-532.
Guilfoyle et al., "Ligation-mediated PCR amplification of specific fragments from a class-II restriction endonuclease total digest," Nucleic Acids Research, 1997, 25:1854-1858.
Haaf et al., "Polymers of N-vinylpyrrolidone: synthesis, characterization, and uses," Polymer J., 1985, 17(1):143-152.
Hall et al., "Sensitive detection of DNA polymorphisms by the serial invasive signal amplification reaction," PNAS, 2000, 97:8272.
Hayden et al., "Multiplex-Ready PCR: A new method for multiplexed SSR and SNP genotyping," BMC Genomics, 2008, 9:80.
Hecker et al., "High and low annealing temperatures increase both specificity and yield in touchdown and stepdown PCR," Biotechniques, 1996, 20(3):478-485.
Herman et al., "Methylation-specific PCR: a novel PCR assay for methylation status of CpG islands," PNAS, 1996, 93(13):9821-9826.
Higuchi et al., "A general method of in vitro preparation and specific mutagenesis of DNA fragments: study of protein and DNA interactions," Nucleic Acids Research, 1988, 16(15):7351-7367.
Higuchi et al.,"Kinetic PCR analysis: real-time monitoring of DNA amplification reactions," Biotechnology, 1993, 11:1026-1030.

(56) References Cited

OTHER PUBLICATIONS

Higuchi et al., "Simultaneous amplification and detection of specific DNA sequences," Biotechnology, 1992, 10:413-417.
Kalinina et al., "Nanoliter scale PCR with TaqMan detection," Nucleic Acids Research, 1997, 25:1999-2004.
Laboratory for Environmental Pathogents Research, Dept of Environmental Sciences, University of Toledo, "Polyvinylpyrrolidone (PVPP) cleanup of DNA samples," Dec. 2004, 2 pages.
Lenntech B.V., "Absolute rating vs. nominal rating for filters," www.lenntech.com/library/fine/absolute/absolute-nominal-filters.htm, retrieved Oct. 3, 2014, 1 page.
Lyamichev et al., "Polymorphism identification and quantitative detection of genomic DNA by invasive cleavage of oligonucleotide probes," Nat. Biotech., 1999, 17:292-296.
Mangiapan et al. "Sequence Capture—PCR Improves Detection of Mycobacterial DNA in Clinical Specimens," Journal of Clinical Microbiology, 1996, 34. p. 1209-1215.
Matteucci et al., "Synthesis of deoxyoligonucleotides on a polymer support," J Am Chem Soc., 1981, 103:3185-3191.
Morgan et al., "Comparison of PCR and microscopy for detection of Cryptosporidium parvum in human fecal specimens: Clinical trial.," J. Clin. Microbiol., 1998, 36(4):995.
Narang et al., "Improved phosphotriester method for the synthesis of gene fragments," Meth Enzymol., 1979, 68: 90-98.
Parham et al., "Specific Magnetic Bead-Based Capture of Genomic DNA from Clinical Samples: Application to the Detection of Group B *Streptococci* in Vaginal/Anal Swabs," Clinical Chemistry, 2007, 53:9, p. 1570-1576.
"PVP in Stool Samples," MadSci Network: Molecular Biology, Nov. 20, 2006.
Qiagen, QIAamp DNA Stool Mini Kit Handbook, Aug. 2001, 40 pages.
QIAamp® genomic DNA Kits, product information, Apr. 2008, 12 pages.
Rehmanji et al., "A novel stabilization of beer with Polyclar Brewbrite," MBAA TQ, 2002, 39(1):24-28.
Roux, "Using mismatched primer-template pairs in touchdown PCR," Biotechniques, 1994, 16(5):812-814.
Schouten et al., "Relative quantification of 40 nucleic acid sequences by multiplex ligation-dependent probe amplification," Nucleic Acids Research, 2002, 30(12): e57.
Shames et al., "Identification of widespread Heliobacter hepaticus infection in feces in commercial mouse colonies by culture and PCR assay," J. Clin. Mocrobiol, 1995, 33(11):2968-72.
Sigma-Aldrich Poly(vinylpolypyrrolidone) product information, retrieved Jun. 26, 2013, 2 pages.
St. John et al., "Rapid capture of DNA targets," BioTechniques, 2008, 44:259-264.
Stone et al., "Detection of rRNA from four respiratory pathogens using an automated Qbeta replicase assay," Mol Cell Probes, 1996, 10:359-370.
Stratagene, Gene Characterization Kits, product information, 1988, 2 pages.
Traverso et al., "Detection of Apc Mutations in Fecal DNA from Patients with Colorectal Tumors," N. Engl. J. Med., 2002, 346(5).
Triglia et al., "A procedure for in vitro amplification of DNA segments that lie outside the boundaries of known sequences," Nucleic Acids Res., 1988, 16:8186.
Verweij et al., "Detection and Identification of Entamoeba Species in Stool Samples by a Reverse Line Hybridization Assay," J Clin Microbiol., 2003, 41(11):5041-5045.
Vogelstein et al., "Digital PCR," PNAS, 1999, 96: 9236-41.
Weiner et al., "Kits and their unique role in molecular biology: a brief retrospective," Biotechniques, 2008, 44:701-704.
Whitney et al., "Enhanced Retrieval of DNA from Human Fecal Samples Results in Improved Performance of Colorectal Cancer Screening Test," JMD, 2004, 6(4).
International Search Report and Written Opinion, dated Apr. 16, 2013, for International Patent IDS filed PCT/US2012/037581, 21 pages.
Zhang et al., "An improved method for purifying genomic DNA from forest leaf litters and soil suitable for PCR", Journal of Soils and Sediments, 2009, vol. 9, No. 3, pp. 261-266.
Glockner et al., "Methylation of TFPI2 in stool DNA: a potential novel biomarker for the detection of colorectal cancer," Cancer Res. Jun. 1, 2009;69(11):4691-9.
Ahlquist et al., "Next Generation Stool DNA Testing for Detection of Colorectal Neoplasia—Early Marker Evaluation", poster presented at Colorectal Cancer: Biology to Therapy, American Association for Cancer Research Conference, Philadelphia, PA Oct. 27-30, 2010, 1 page.
Ahlquist et al., "Next-generation stool DNA test accurately detects colorectal cancer and large adenomas." Gastroenterology, 2012, 142:248-56.
Zou et al., Highly methylated genes in colorectal neoplasia: implications for screening. Cancer Epidemiol Biomarkers Prev. Dec. 2007;16(12):2686-96.

\* cited by examiner

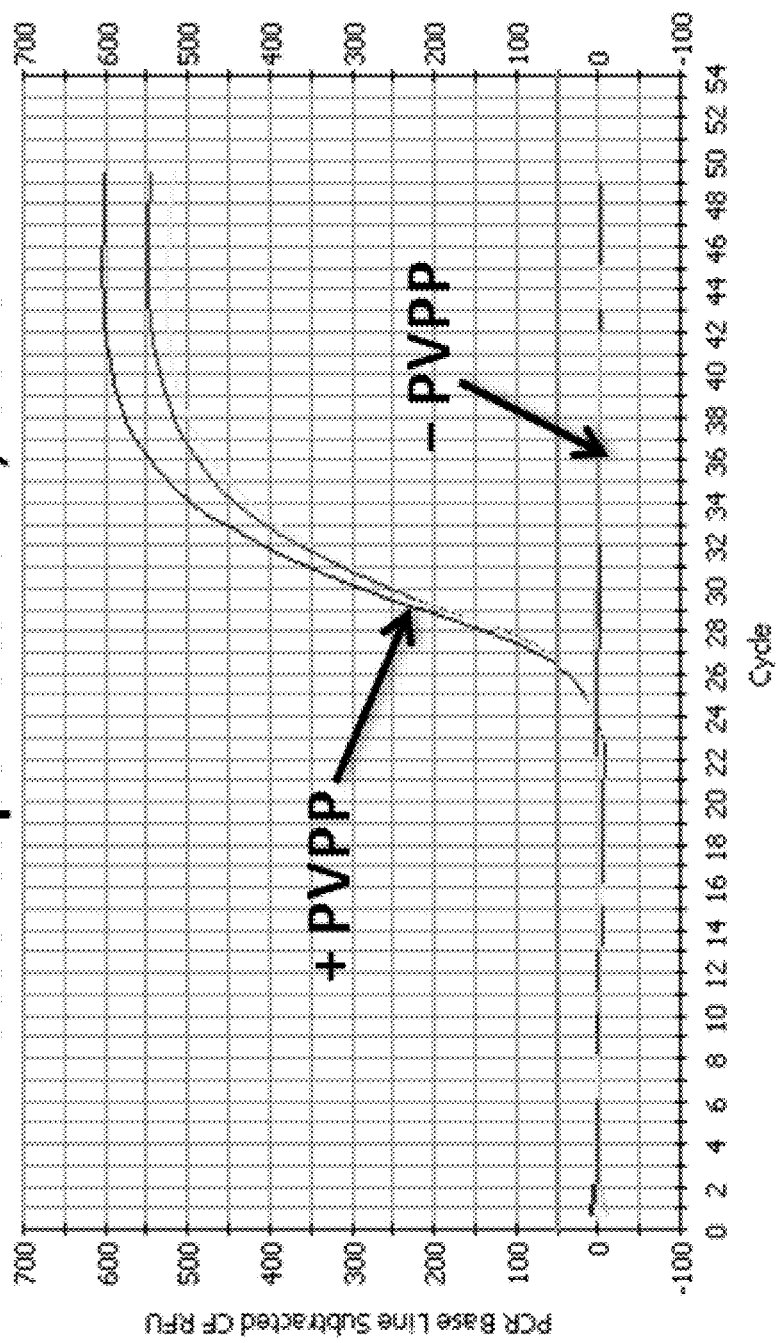

REMOVAL OF PCR INHIBITORS

The present application is a Continuation of copending U.S. patent application Ser. No. 13/469,989, filed May 11, 2012, which claims the benefit of U.S. Provisional Patent Application Ser. No. 61/485,338, filed May 12, 2011, each of which is incorporated herein by reference in its entirety.

FIELD OF INVENTION

Provided herein is technology relating to processing and preparing samples and particularly, but not exclusively, to methods, devices, systems, and kits for removing assay inhibitors from samples comprising nucleic acids.

BACKGROUND

Medical diagnostics are increasingly incorporating nucleic acid-based assays. Such assays include, e.g., qualitative measurements of the absence or presence of a nucleic acid (i.e., various forms of DNA and RNA), quantitative measurements of the amount of a nucleic acid in a biological sample, and determinations of the physical characteristics or modification state of a nucleic acid. However, biological materials are often contaminated with substances that damage nucleic acids during storage or inhibit enzymatic manipulation of the nucleic acids, e.g., digestion with restriction enzymes or amplification by polymerase chain reaction (PCR). Therefore, to use the nucleic acids isolated from certain biological materials for further analysis, it is important that the amounts of these inhibiting substances should be minimized, i.e., they should be present only in very low concentrations or in some cases should be eliminated entirely from the sample.

Purifying nucleic acids from biological samples commonly uses a combination of different purification steps such as protease treatment, phenol/chloroform extraction, binding of nucleic acids to silica in the presence of chaotropic salts, gel filtration, anion exchange chromatography, and the use of cationic or anionic detergents. Nucleic acids isolated from biological samples by these methods are, however, often unstable and behave problematically in subsequent enzymatic reactions such as PCR, for example. Many of these problems arise due to the presence of substances that are co-isolated with the nucleic acids and that damage them and inhibit enzymatic reactions. Examples of these inhibitors from biological sources include hemoglobin and its metabolites, bile acids and bile acid derivatives, and polysaccharides.

These substances are especially problematic for assays directed to measuring rare events, e.g., rare mutations or other rarely occurring genetic modifications. Assays designed to detect low-incidence events are vulnerable to inhibitors for at least two related reasons. Highly sensitive assays designed to detect extremely small amounts of nucleic acids may be compromised by trace amounts of inhibitors. Also, such assays require large amounts of a nucleic acid for analysis and thus often the assays will also include substantial amounts of the co-purified inhibitors.

Others have attempted to solve this problem using a variety of techniques. Most conventional methods first employ a total nucleic acid precipitation step followed by inhibitor removal or inactivation using proprietary adsorption resins and optimized buffers. These methods, though, are not applicable to all samples and assays because, while some inhibitors are soluble and thus can be separated from the nucleic acid preparation in these methods, a large number of inhibitors co-precipitate with the nucleic acid preparation.

Moreover, many highly sensitive assays require maximizing the volume of isolated nucleic acids that comprise the assay volume, e.g., by using a large sample as input and concentrating the nucleic acid sample into a small volume. Conventional solutions, though, do not function adequately when scaled up for processing large samples. They either cannot accommodate large samples or are not sufficiently effective on the large samples. When even relatively small amounts of inhibitors remain, only a very limited amount of the isolated nucleic acid can be used in subsequent assays without inhibiting a subsequent assay or other reaction. Consequently, the amount of material that can be added to the assay is insufficient to reach the sensitivity limits of some assays.

SUMMARY

As a result of these problematic aspects of the conventional technology, what is needed is a low-cost, simple, and time-efficient inhibitor removal method. In particular, there is a need for such methods that are appropriate for processing large biological samples comprising inhibitors. Nucleic acids are often the input for sensitive genetic tests. For many of these tests, to have sufficient template to detect rare events, captured nucleic acids comprise a significant fraction (e.g., one-third) of the assay volume. However, many samples contain a wide variety of different compounds that are inhibitory to diagnostic assays. Thus, the extraction procedures include methods to remove and/or inactivate inhibitors.

Accordingly, provided herein is technology relating to processing and preparing samples and particularly, but not exclusively, to methods, systems, and kits for removing assay inhibitors from samples comprising nucleic acids. For example, provided herein are methods for removing an assay inhibitor from a crude sample preparation comprising a nucleic acid, the method comprising adding an insoluble polyvinylpyrrolidone to the crude sample preparation prior to isolating the nucleic acid; binding the assay inhibitor, if present, to the polyvinylpyrrolidone to produce a complex; separating the complex from the crude sample preparation; and retaining the crude sample preparation comprising the nucleic acid. The technology is not limited in the types of samples that can be processed by the methods provided herein. For example, in some embodiments the crude sample preparation is a supernatant prepared from a stool sample. In some embodiments the stool sample has a mass of at least 4 grams and in some embodiments the stool sample has a mass of at least 8 grams. In some embodiments of the method, the polyvinylpyrrolidone is a polyvinylpolypyrrolidone. While the methods contemplate many different types and sizes of polyvinylpyrrolidone, in some embodiments the polyvinylpyrrolidone comprises particles having a diameter averaging from 100-130 micrometers.

The technology is not limited in the methodology that can be used for the separating step. For example, in some embodiments of the technology a spin column is used for the separating step. Spin columns are widely available in many useful configurations. In certain embodiments, a clog-resistant spin filter as provided in U.S. Pat. Appl. Ser. No. 61/485,214 is used. For example, in some embodiments, the technology makes use of a spin filter comprising a hollow body, a bottom end, and an open top end opposite the bottom end, wherein the hollow body is made from a porous filtering material. In some preferred embodiments, the bottom end is made from a porous filtering material.

In some embodiments, a conventional spin column is used that comprises a polyethylene frit, e.g., a frit having a nominal pore size of 20 micrometers (the actual pore size varies somewhat between approximately 15 to approximately 40 micrometers). Additional embodiments provide that the separating step comprises centrifuging. In some embodiments the separating step comprises centrifuging at 3200×g for 6 minutes. For example, in some embodiments providing a spin column, the spin column is centrifuged at 3200×g for 6 minutes.

The technology is directed to minimizing the amount of an inhibitor in a sample. For example, the methods provide a technology for removing inhibitors such that the resulting concentration is below a threshold level that can inhibit certain assays. As such, in some embodiments, the retained sample preparation comprises a first amount of the assay inhibitor that is less than a second amount of the assay inhibitor, wherein the second amount of the assay inhibitor inhibits PCR when 5 microliters of the retained sample preparation are used in a PCR having a volume of 25 microliters. That is, the method provides a way to prepare a sample from which 5 microliters can be used in a subsequent assay without there being present in the assay sufficient inhibitors to inhibit the assay. In some embodiments, the retained sample preparation comprises a first amount of the assay inhibitor that is less than a second amount of the assay inhibitor, wherein the second amount of the assay inhibitor inhibits PCR when 1 microliter of the retained sample preparation is used in a PCR having a volume of 25 microliters. That is, the method provides a way to prepare a sample from which 1 microliter can be used in a subsequent assay without there being present in the assay sufficient inhibitors to inhibit the assay.

The technology provided herein can also be embodied in a system for processing samples. For example, embodiments provide a system for removing an assay inhibitor from a crude sample preparation comprising a nucleic acid, the system comprising insoluble polyvinylpyrrolidone for binding the assay inhibitor and producing a complex; functionality for separating the complex from the crude sample preparation; and functionality for retaining the crude sample preparation comprising the nucleic acid. In some embodiments, the crude sample preparation is a supernatant prepared from a stool sample. In some embodiments the stool sample has a mass of at least 4 grams and in some embodiments the stool sample has a mass of at least 8 grams. In some embodiments of the system provided, the polyvinylpyrrolidone is a polyvinylpolypyrrolidone. In some embodiments, the polyvinylpyrrolidone comprises particles having a diameter averaging from 100-130 micrometers.

The system is not limited in the means by which the inhibitor-bound complex is removed from the sample. In some embodiments, the functionality for separating the complex from the crude sample preparation comprises a spin column or spin filter. Various types of spin columns are appropriate for the methods described. For example, some embodiments of the methods provided benefit from using a spin column comprising a polyethylene frit, e.g., having a nominal pore size of 20 micrometers. It is also contemplated that a clog-resistant spin filter (e.g., as described in U.S. Pat. Appl. Ser. No. 61/485,214) finds use in the methods described. In some embodiments the functionality for separating the complex from the crude sample preparation comprises centrifuging. For example, in some embodiments the separating step comprises centrifuging at 3200×g for 6 minutes and in some embodiments employing a spin column the spin column is centrifuged at 3200×g for 6 minutes.

In some embodiments, the retained sample preparation comprises a first amount of the assay inhibitor that is less than a second amount of the assay inhibitor, wherein the second amount of the assay inhibitor inhibits PCR when 5 microliters of the retained sample preparation are used in a PCR having a volume of 25 microliters. In some embodiments, the retained sample preparation comprises a first amount of the assay inhibitor that is less than a second amount of the assay inhibitor, wherein the second amount of the assay inhibitor inhibits PCR when 1 microliter of the retained sample preparation is used in a PCR having a volume of 25 microliters.

Furthermore, herein are provided kits for removing an assay inhibitor from a crude sample preparation comprising a nucleic acid, the kit comprising insoluble polyvinylpyrrolidone; a spin column; and an instruction for use. Various types of spin columns are available for inclusion in a kit, for example those commercially available from a number of suppliers. For some inhibitor-removal applications, it is advantageous to include a clog-resistant spin filter such as described in U.S. Pat. Appl. Ser. No. 61/485,214. The kits are not limited in the types of samples for which they can be used. For example, in some embodiments the crude sample preparation is a supernatant prepared from a stool sample. In some embodiments, the stool sample has a mass of at least 4 grams and in some embodiments the stool sample has a mass of at least 8 grams.

In some embodiments the polyvinylpyrrolidone is a polyvinylpolypyrrolidone. In some embodiments, the polyvinylpyrrolidone comprises particles having a diameter averaging from 100-130 micrometers. Moreover, in some embodiments the spin column comprises a polyethylene frit. In some embodiments the polyethylene frit has a nominal pore size of 20 micrometers (the actual sizes of the pores are distributed from approximately 15 micrometers to approximately 40 micrometers). In some embodiments the kits further comprise a primer or a probe for analysis of the isolated nucleic acid.

Also provided herein are methods for filtering samples comprising placing a sample to be filtered into the spin filter and centrifuging the spin filter. In some embodiments the method comprises recovering the filtrate. The technology can be provided as a kit for use in a sample separation. Embodiments of such a kit comprise a spin filter and an instruction for use. In some embodiments the kit further comprises a collection vessel.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 5A is a drawing of a disc-shaped, solid (e.g., non-porous or non-permeable) bottom end; FIG. 5B is a drawing of a disc-shaped, porous (permeable) bottom end; FIG. 5C is a drawing of a porous, conical bottom end.

FIG. 8A is an assembled view and FIG. 8B is an exploded view.

FIGS. 9A-9D are plots showing the removal of inhibitors from a stool sample.

DETAILED DESCRIPTION

Figure 1:
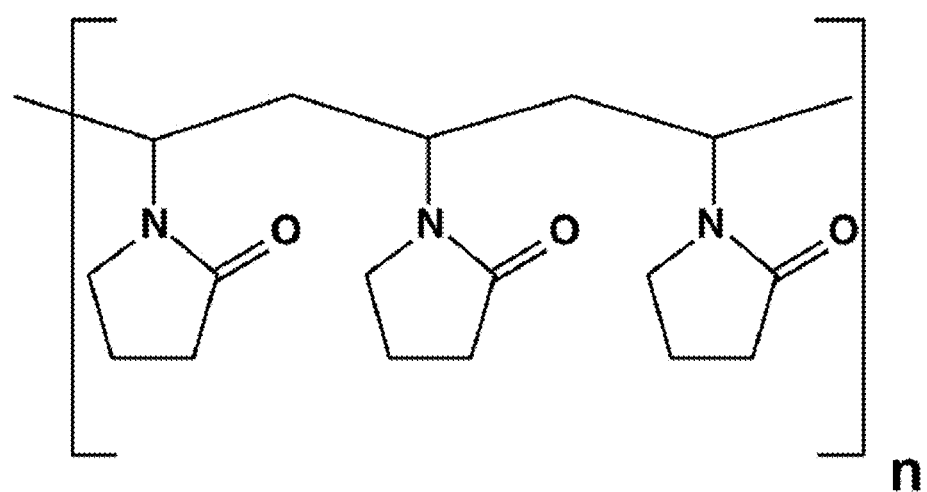
FIG. 1 is a chemical structure of a polyvinylpyrrolidone.

One goal of medical diagnostics is to extract sequence-specific human DNA directly from a large volume of stool for use in a quantitative assay. Such a sample finds use in assays directed to, for example, measurement of mutation or methylation levels of target genes as a screen for colon cancer and/or adenoma. To have sufficient template to detect rare mutation or methylation events in some sensitive assays, the captured DNA comprises a substantial portion of the assay reaction volume (e.g., in some assays approximately one-fifth to one-fourth of the assay reaction volume). However, biological samples, such as stool samples, contain a wide variety of different compounds that are inhibitory to PCR. Thus, the DNA extraction procedure includes methods to remove and/or inactivate PCR inhibitors. As such, provided herein is technology relating to processing and preparing samples and particularly, but not exclusively, to methods, systems, and kits for removing assay inhibitors from samples comprising nucleic acids.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, an "inhibitor" means any compound, substance, composition, or combination thereof, that acts to decrease the activity, precision, or accuracy of an assay, either directly or indirectly, with respect to the activity, precision, or accuracy of the assay when the inhibitor is absent. An inhibitor can be a molecule, an atom, or a combination of molecules or atoms without limitation.

As used herein, the process of passing a mixture through a filter is called "filtration". The liquid produced after filtering a suspension of a solid in a liquid is called "filtrate", while the solid remaining in the filter is called "retentate", "residue", or "filtrand".

As used herein, "insoluble" refers to the property that a substance does not substantially dissolve in water and is essentially immiscible therewith. Upon separation of an aqueous phase from a non-aqueous phase, an insoluble substance does not partition into or partition with the aqueous phase.

As used herein, the terms "subject" and "patient" refer to any animal, such as a mammal like a dog, cat, bird, livestock, and preferably a human.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849, 481, 5,710,264, 5,124,246, and 5,624,802, herein incorporated by reference in their entireties); rolling circle replication (e.g., U.S. Pat. Nos. 6,210,884, 6,183,960 and 6,235, 502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S.

Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication US 20090253142 A1 (application Ser. No. 12/404,240), incorporated herein by reference in its entirety for all purposes. Additional amplification plus invasive cleavage detection configurations, termed the QuARTS method, are described in U.S. patent application Ser. Nos. 12/946,737; 12/946,745; and 12/946,752, incorporated herein by reference in their entireties for all purposes.

The term "invasive cleavage structure" as used herein refers to a cleavage structure comprising i) a target nucleic acid, ii) an upstream nucleic acid (e.g., an INVADER oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

Embodiments of the Technology

Although the disclosure herein refers to certain illustrated embodiments, it is to be understood that these embodiments are presented by way of example and not by way of limitation.

1. Polyvinylpyrrolidone

Polyvinylpyrrolidone (PVP) is a water-soluble polymer made from the monomer N-vinylpyrrolidone (see FIG. 1). Polyvinylpolypyrrolidone (PVPP) is a highly cross-linked modification of PVP. The extent of cross-linking can vary and there is no defined threshold establishing a division between PVP and PVPP. Accordingly, the term PVP is used herein to refer to PVP in various states of cross-linked polymerization, including preparations of PVP that may also be known in the art as PVPP. An important property, however, is that as the extent of cross-linking is increased, the polymer becomes increasingly insoluble in water. The cross-linked forms absorb water, which causes the polymer to swell. The synthesis and physical properties of PVP and PVPP are well-known in the art (e.g., see Haaf, Sanner, & Straub. *Polymers of N-vinylpyrrolidone: synthesis, characterization, and uses*. Polymer J. 17(1): 143 (1985)).

PVP has been used in many technical applications including use as a blood plasma expander; as a binder in many pharmaceutical tablets; as an adhesive in glue stick and hot melts; as an additive for batteries, ceramics, fiberglass, inks, inkjet paper and in the chemical-mechanical planarization process; as an emulsifier and disintegrant for solution polymerization; as photoresist; for production of membranes, such as dialysis and water purification filters; as a thickening agent in tooth whitening gels, etc.

PVP has also found use in binding impurities and removing them from solutions, particularly in wine-making and beer-making to remove polyphenols (see, e.g., Redmanji, Gopal, & Mola. *A novel stabilization of beer with Polyclar Brewbrite*. MBAA TQ 39(1): 24 (2002)). The use of soluble and insoluble forms of PVP has been described in relation to processing biological samples as a means to neutralize phenols (see, e.g., U.S. Pat. No. 7,005,266; Shames, et al. *Identification of widespread Helicobacter hepaticus infection in feces in commercial mouse colonies by culture and PCR assay*. J. Clin. Microbiol. 33(11): 2968 (1995); Morgan et al. *Comparison of PCR and microscopy for detection of Cryptosporidium parvum in human fecal specimens: Clinical trial*. J. Clin. Microbiol. 36(4): 995 (1998)).

The PVP is provided in forms that allow its introduction into a sample that is to be processed, e.g., as a powder, slurry, suspension, in granules, and the like. In some embodiments of the technology provided herein, the PVP is provided premeasured in a ready-to-use form. For example, in some embodiments, the PVP is pressed into a tablet comprising the mass of PVP appropriate for treating a sample. Different sizes and shapes of tablets are provided for different volumes and types of samples. Inert binders, fillers, and other compositions may be added to the tablets to provide physical, thermal, chemical, and biological stability, or to provide other desired characteristics such as improved dispersion within the sample or controlled-release.

2. Samples

The sample containing nucleic acids is obtained from materials that contain impurities that break down nucleic acids or inhibit enzymatic reactions. In particular, impurities of this kind inhibit the enzymatic activity of restriction enzymes and other enzymes, e.g., those that are used for polymerase chain reaction (PCR) and various types of nucleic acid detection assays. For example, the sample may be fecal material. However, the sample may also be obtained from other sources, e.g., animal or plant tissues; tissue or cell cultures; bone marrow, human, and animal body fluids such as blood, serum, plasma, urine, semen, cerebrospinal fluid, sputum, and smears; plants, parts of plants, and plant extracts, e.g., saps, fungi, prokaryotic or eukaryotic microorganisms such as bacteria or yeasts, fossilized or mummified samples, soil samples, clarified sludge, sewage, and foodstuffs (particularly processed, i.e., industrially prepared foodstuffs). The samples may contain water-insoluble ingredients.

3. Inhibitors

The sample may be a sample of material that contains impurities that break down nucleic acids or inhibit enzymatic reactions. In particular, such impurities inhibit the enzymatic activity of enzymes that interact with nucleic acid, e.g., nucleases such as restriction endonucleases, reverse transcriptases, nucleic acid polymerases, ligases, etc., particularly enzymes which are used for polymerase chain reaction (PCR), LCR (ligase chain reaction), NASBA (nucleic acid base specific amplification), 3SR (self sustained sequence replication), and the like.

4. Methods, Devices, Systems, and Kits

Figure 2:
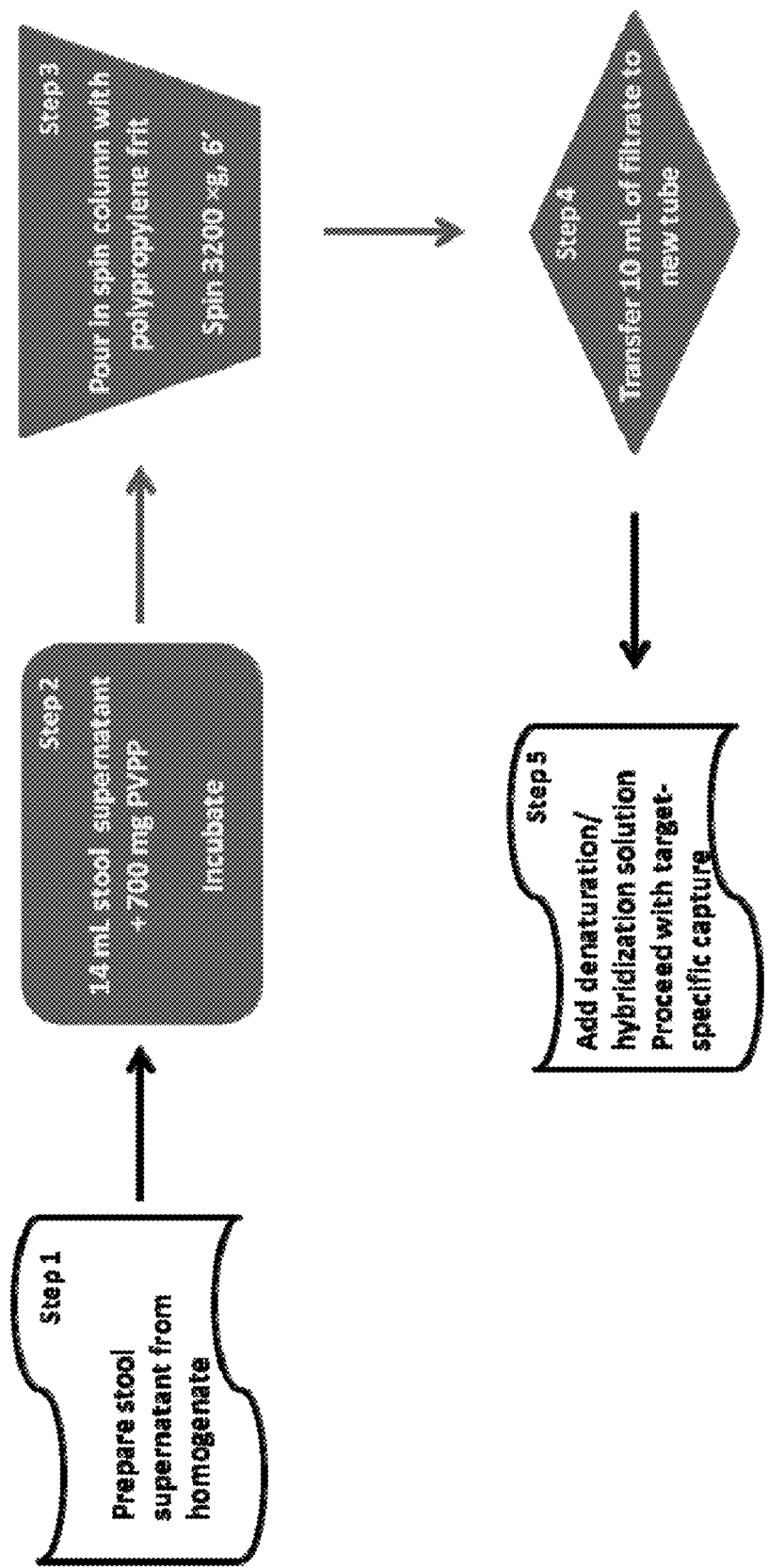
FIG. 2 is a flowchart of the inhibitor removal method.

The technology provided herein relates to the use of PVP to remove inhibitors from biological samples. An embodiment of the methods as applied to a stool sample is provided in FIG. 2. First, a stool sample is homogenized and centrifuged to prepare a stool supernatant. The methods are particularly appropriate for processing large samples, e.g., having a mass greater than 1 gram, having a mass greater than 4 grams, and having a mass of 8 grams or more. Then, 700 milligrams of PVP are added to 14 milliliters of the stool supernatant to produce a final concentration of approximately 50 milligrams per milliliter PVP. The suspension is mixed and incubated (e.g., at ambient temperature, at 22° C., at 37° C.) to bind inhibitors, e.g., for 15 minutes. The suspension is then filtered using a spin column, either one of conventional design or a clog-resistant spin filter such as is provided in U.S. Pat. Appl. Ser. No. 61/485,214 of Domanico et al., (incorporated herein by reference in its entirety for all purposes). After pouring the suspension into a spin column, optionally comprising a polyethylene frit (e.g., having a nominal pore size of 20 micrometers), to collect the PVP, the spin column is centrifuged at 3200×g for 6 minutes. A volume of 10 milliliters of the filtrate is removed from the spin column collection space for further processing and assay.

Both the degree of cross-linking and the size of the PVP particles are parameters affecting the downstream assay of the resulting nucleic acid preparations. For example, soluble PVP has been found to inhibit some downstream assays. Accordingly, the method benefits from using a PVP that is sufficiently insoluble (e.g., sufficiently cross-linked) to allow adequate removal of the PVP by downstream processing steps (e.g., spin filtration). In addition, when the cross-linked PVP particles are too small they pack too tightly in the spin column and restrict the effluent flow of the sample into the spin column collection space. For example, experiments performed during the development of some embodiments of the present technology demonstrated that a PVP having an average particle size of approximately 100-130 micrometers produced satisfactory results while a particle size of approximately 30-50 micrometers restricted flow. Further experimentation may indicate that other sizes and solubilities may be appropriate for the method.

Figure 3:
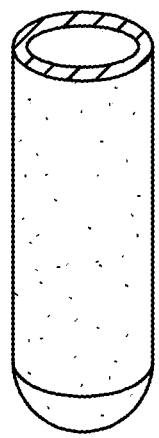
FIG. 3 is a drawing of one type of a spin filter that finds use in the methods, systems, and kits provided herein.
Figure 4:
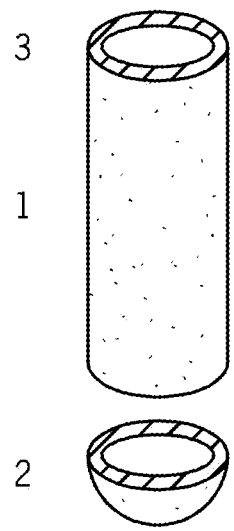
FIG. 4 is a drawing showing an exploded view of the spin filter shown in FIG. 3.
Figure 5A:
FIGS. 5A-C are a series of drawings showing various types of bottom ends that a spin filter may comprise.
Figure 5B:
Figure 5C:
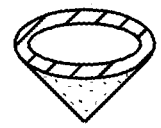

The technology provided herein benefits from a wide range of a spin filters that are used, for example, to filter samples treated with PVP. As discussed above, during the development of the PVP treatment method, experiments demonstrated that some conventional spin columns having a filter frit in the bottom end clogged under some conditions. Accordingly, a clog-resistant spin filter finds use in the methods described herein. One example of a clog-resistant spin filter described by Domanico, supra, is shown for reference in FIGS. 3 and 4. The spin filter shown in FIGS. 3 and 4 is a spin filter comprising a tubular (hollow cylindrical) body and a hemi-spherical bottom end and FIG. 5 shows other shapes and configurations of the spin filter. For example, one configuration that is useful for filtering PVP is one in which the bottom end is a non-porous disc (e.g., FIG. 5A) and the body is made from a porous material and provides the filtration medium. In another variation, both the body and the bottom end are made from a porous material and thus both act to filter the sample. The clog-resistant spin filter technology is designed to allow the sample to be filtered through the body walls if the bottom end becomes clogged with residue removed from the sample.

Figure 6:
FIG. 6 is a drawing of a spin filter assembled with a collection tube
Figure 7:
FIG. 7 is a cut-away drawing of the spin filter depicted it FIG. 6.
Figure 8A:
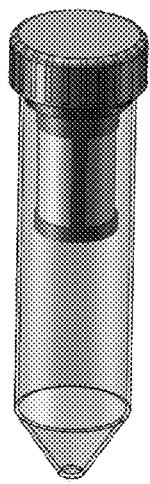
FIGS. 8A and 8B are drawings of a spin filter and a filter support.
Figure 8B:
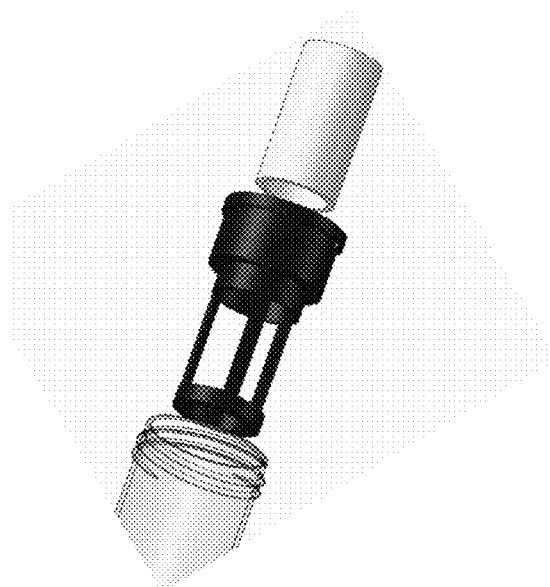

FIGS. 6 and 7 show the spin filter depicted in FIGS. 3 and 4 assembled with a collection vessel. This arrangement allows the capture of the filtrate in the collection tube for retention or additional processing. FIG. 8 shows a spin filter in which the bottom is provided by a filter support made from a non-porous material. The filter body is inserted into the filter support and a fluid-tight seal is formed between the body and filter support.

Spin filters are made from a variety of materials. The spin filters that find use in the technology provided herein are made from a material that provides for filtration of a sample while also being inert with respect to the sample—that is, the material does not react with or otherwise contaminate or modify the sample, other than filtering it, in a way that affects a subsequent assay, causes its degradation, causes its decomposition, or the like. For example, some filters are made from polyethylene and others are made from nylon, cellulose-acetate, polytetrafluoroethylene (PTFE, also known as Teflon), polyvinylidene fluoride (PVDF), polyester, and polyethersulfone. Operating pressure, the chemical and physical characteristics of the composition to be filtered, the size of the entity to remove from the sample, and the mechanical properties of the material (e.g., capability to withstand centrifugation at the speed required for the filtering application) are factors that are considered when selecting the spin filter material.

Moreover, filters may have pore sizes appropriate for many types of filtering applications. For example, a filter with pore size of 0.2 micrometers will effectively remove most bacteria while smaller pore sizes are required to remove viruses and bacterial spores. For removing larger particulates, a larger pore size is adequate. For example, some embodiments of the technology provided herein benefits from the use of a spin filter having a 20-micrometer pore size. Other pore sizes that find use in filtration applications are 0.22, 0.45, 10, 20, 30, and 45 micrometers. Larger and smaller pore sizes are contemplated, as well as pore sizes intermediate within the intervals delimited by these values. For some filtration applications the filter is characterized by the molecular weight of the molecules that are retained by the filter. For example, a filter with a 5,000 Da molecular weight cutoff (MWCO) will retain molecules and complexes having at least a molecular weight of approximately 5,000 Da. Filters can provide MWCOs of 10,000 Da; 30,000 Da; 50,000 Da; 100,000 Da, and other limits required for the filtration task. Operating pressure and the size of the entity to remove from the sample are factors to consider when choosing a pore size or cutoff value.

In another aspect, the methods and devices provided find application in various kits and systems designed for convenient use by a user. For example, it is contemplated to provide kits comprising premeasured, sterilized, and packaged PVP and an appropriate spin column, e.g., a conventional spin column optionally comprising a polyethylene frit or a clog-resistant spin filter as described by Domanico, supra. Some kits further provide instructions for processing a sample. Such a kit optionally comprises buffers and other reagents that are necessary to process the samples and produce a nucleic acid suitable for assay. The buffer may be present in a finished form, as a concentrate, or in a lyophilized form. The kits and systems may optionally contain additional means for purifying nucleic acids which comprise, for example, inorganic and/or organic carriers and optionally solutions, excipients, and accessories. Such components are known in the art and are commercially available.

The kit may optionally comprise a primer or probe for amplifying or detecting the isolated nucleic acid. The nucleic acid is preferably derived from the genes which are to be analyzed (e.g., from oncogenes, tumor suppressor genes, and/or micro-satellites) or they may be suitable for amplifying viral or bacterial nucleic acid sequences. Enzymes and restriction endonucleases suitable for amplifying nucleic acids are known and commercially available. Furthermore, the PVP may be provided in a premeasured form, e.g., as a tablet or in granules as described above.

Also contemplated are systems for processing nucleic acids. The systems provide functionalities for adding PVP to a sample to bind inhibitors, separating the PVP and bound inhibitors from the sample, and retaining the isolated nucleic acid for additional processing as described herein.

EXAMPLES

Example 1

Figure 9A:
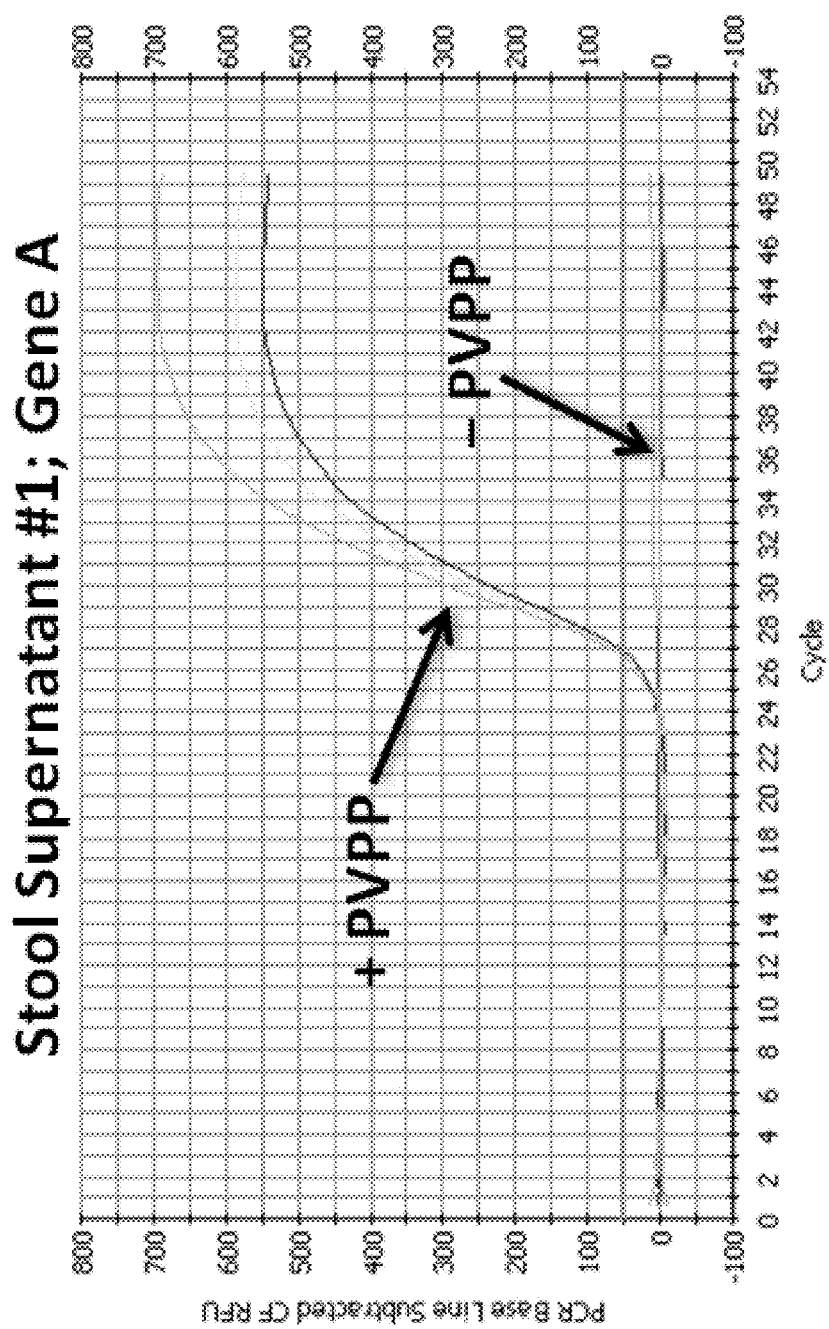
Figure 9B:
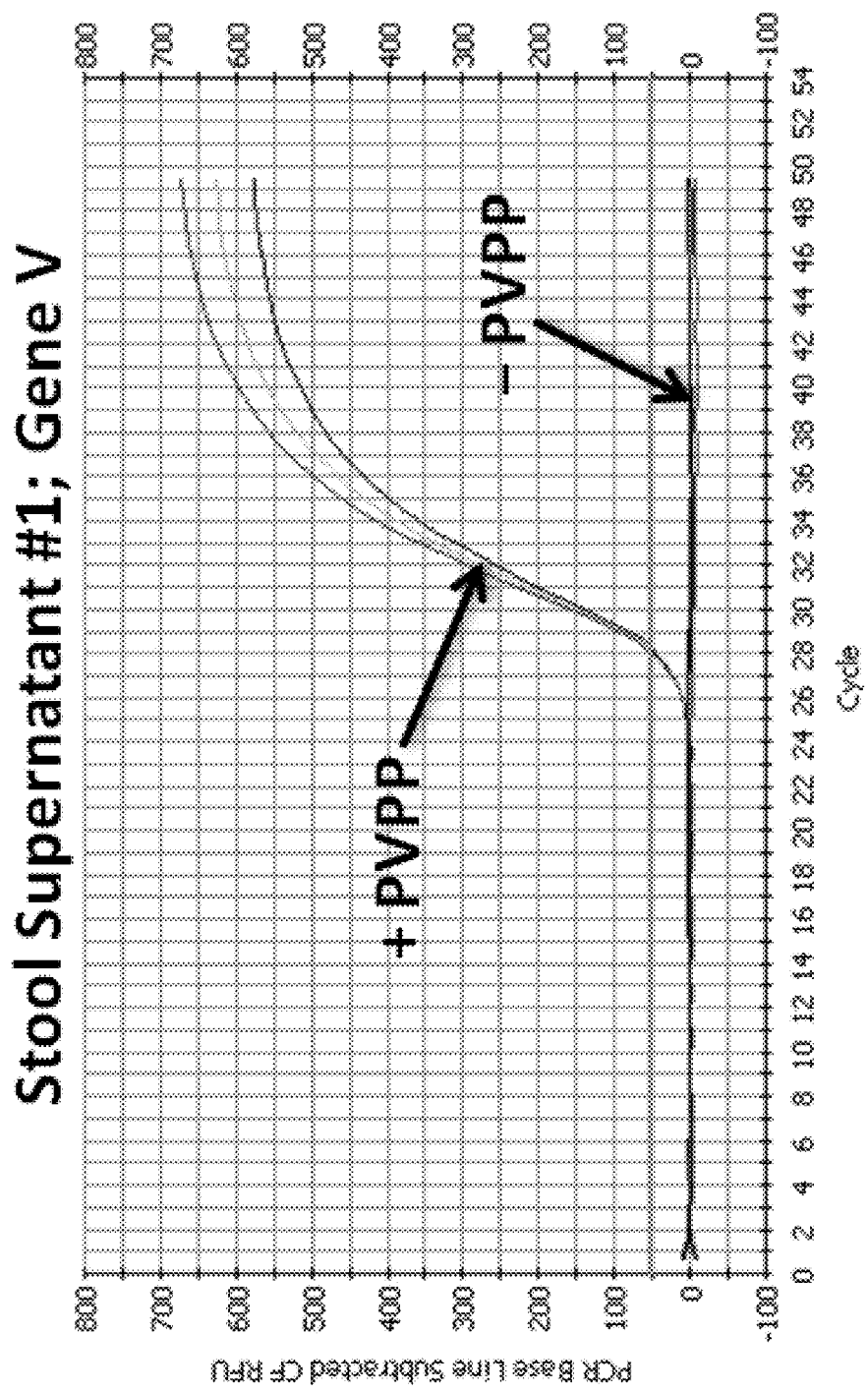
Figure 9D:
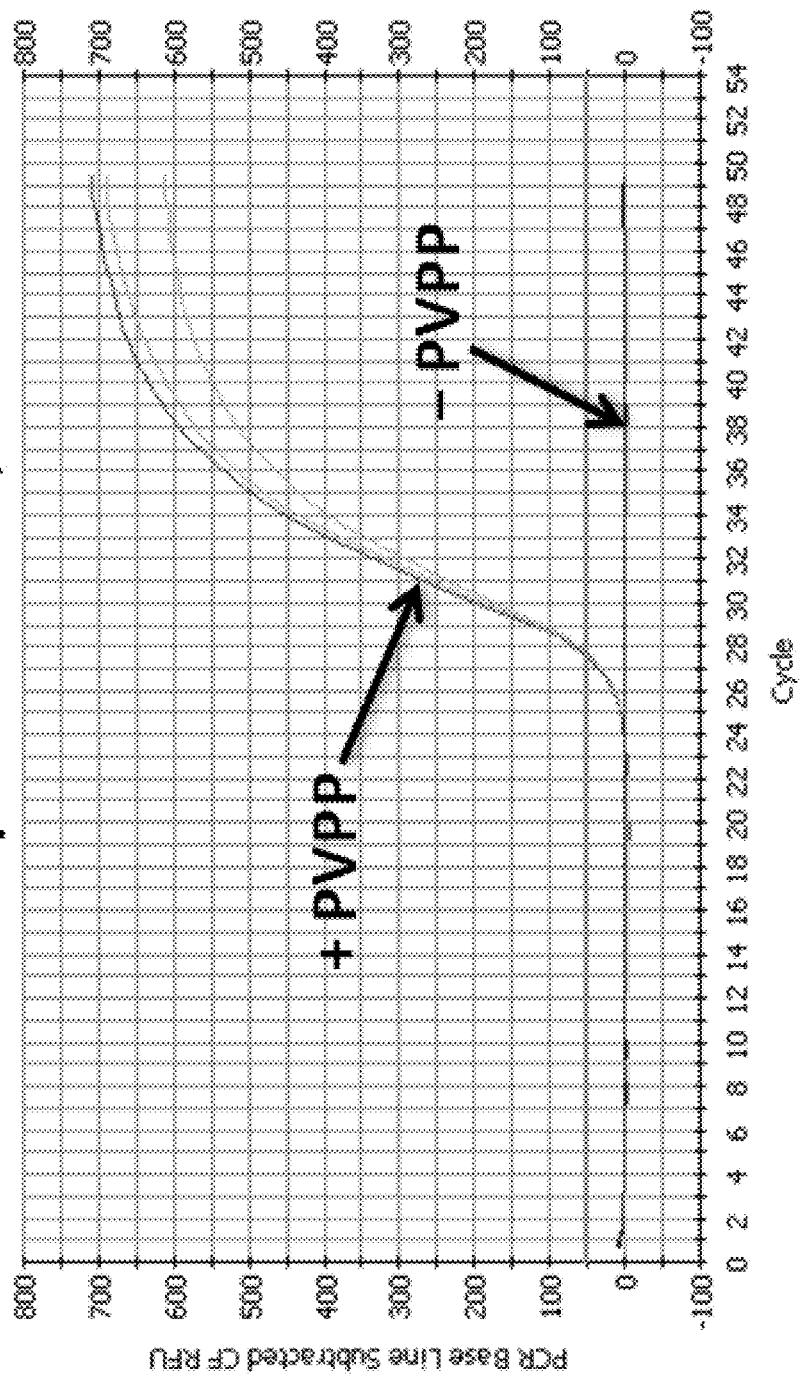

During the development of embodiments of the technology provided herein, it was demonstrated that PVP removes PCR inhibitors from a stool sample (see FIG. 9). Volumes of 20 milliliters were taken from the supernatants of two different stool supernatant samples. For each stool sample, one aliquot was treated with PVP and the other was left untreated. Otherwise, the samples were processed identically to capture two different nucleic acid targets (FIG. 9, Gene A and Gene V). After capture and final elution, the recoveries of the two targets were monitored by a SYBR Green quantitative PCR (qPCR) assay using 1 microliter of eluate in a 25 microliter reaction volume. For both targets from both stool supernatants, aliquots treated with PVP were amplified whereas the untreated aliquots failed to produce any qPCR signal. These results demonstrate the necessity and efficacy of PVP as an inhibitor-removal treatment when extracting DNA from stool samples for assay by a quantitative PCR assay.

Example 2

Figure 10A:
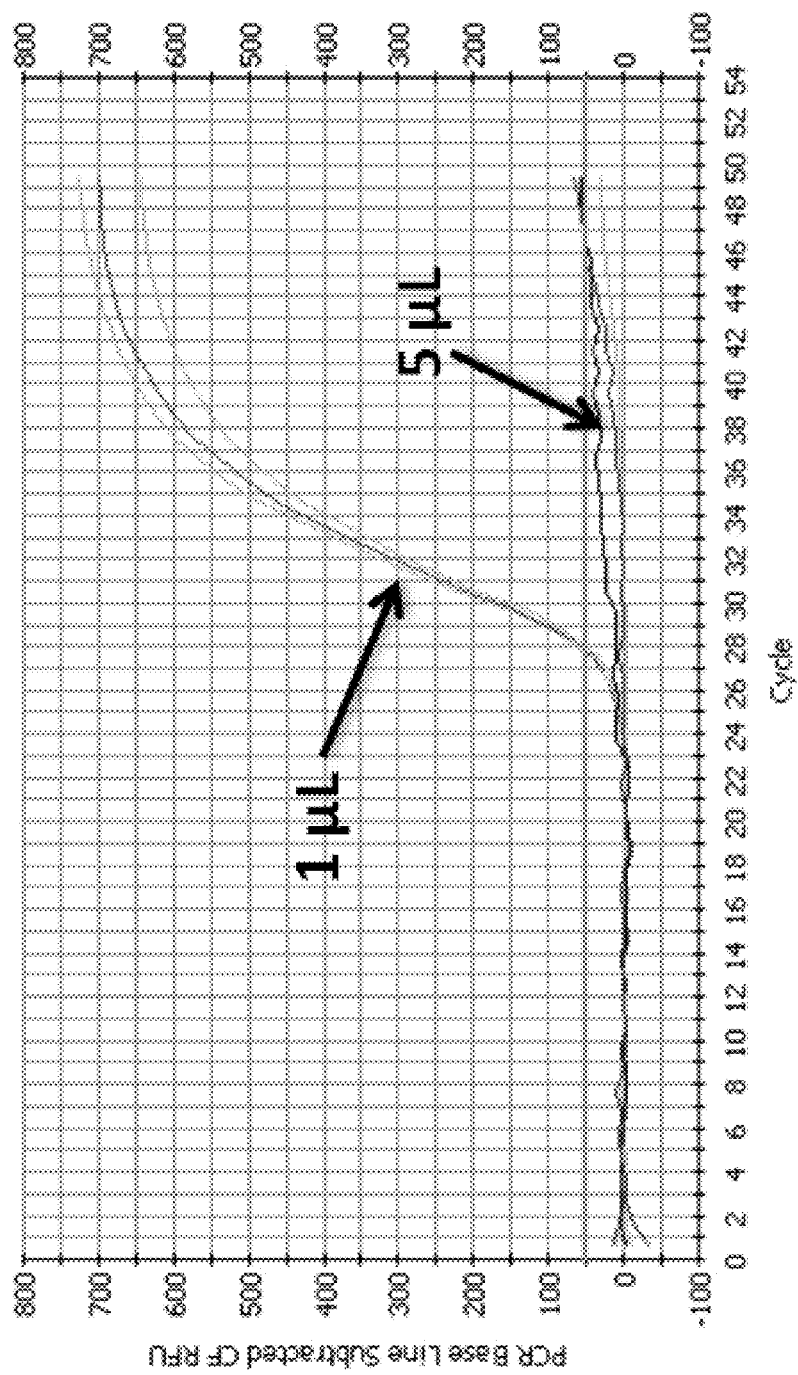
FIGS. 10A-10D are plots showing that spin filtration improves the removal of inhibitors.
Figure 10B:
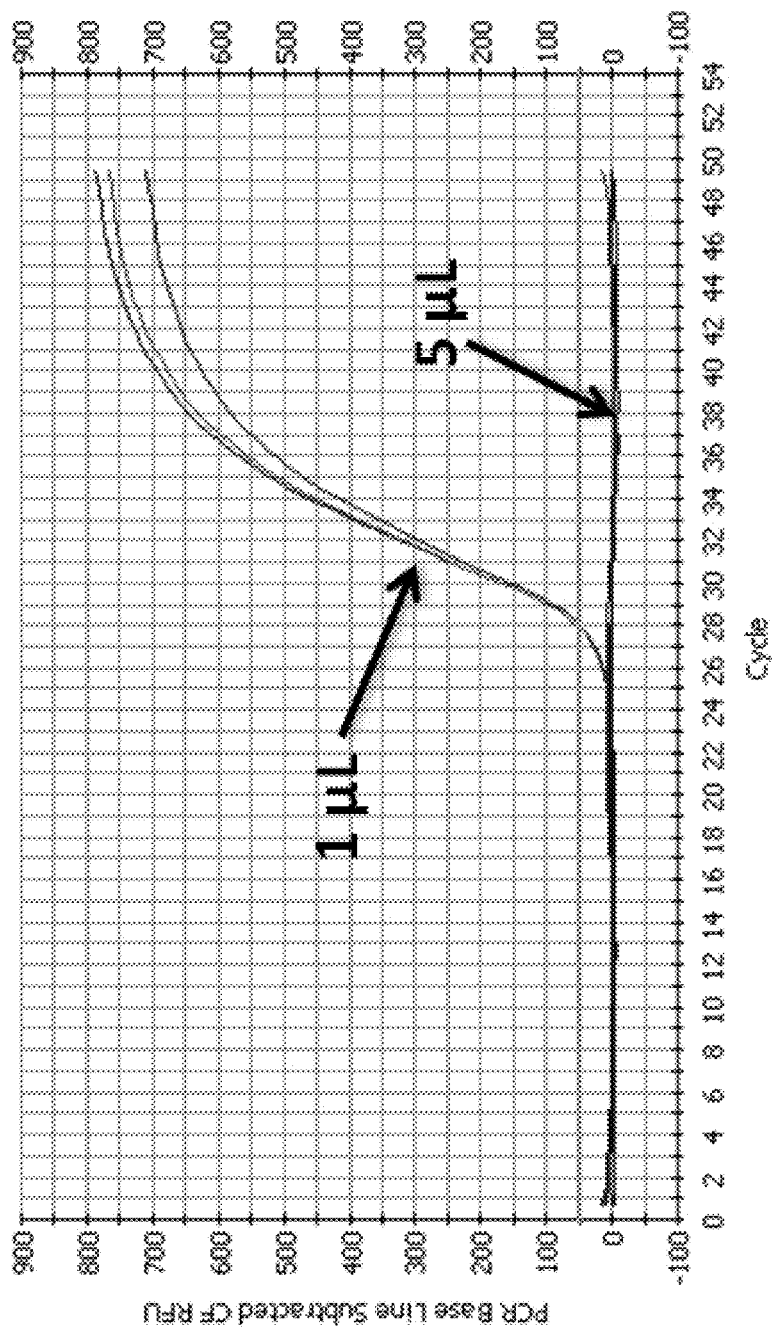

During the development of embodiments of the technology provided herein, data were collected demonstrating that spin filtering improves the removal of PCR inhibitors. The experiment compared PVP of different sizes for the ability to remove PCR inhibitors from stool supernatant samples. Two commercially available PVP compositions were compared: Polyclar® 10 and Polyplasdone® XL, which are composed of PVP particles having an average diameter of 30-50 micrometers and 100-130 micrometers, respectively. Inhibitor removal by the two PVP compositions was assessed by qPCR in which 1 microliter or 5 microliters of the isolated DNA eluates were used in a 25-microliter reaction volume. First, both types of PVP were separated from the stool supernatant by pelleting (centrifugation). For both PVP types, samples showed equal recovery and amplification curve shape when 1 microliter of eluted DNA was added to the qPCR. However, using 5 microliters of eluate failed to produce any qPCR signal, indicating that PCR inhibitors remained in the sample (see FIGS. 10A and 10B).

Figure 10C:
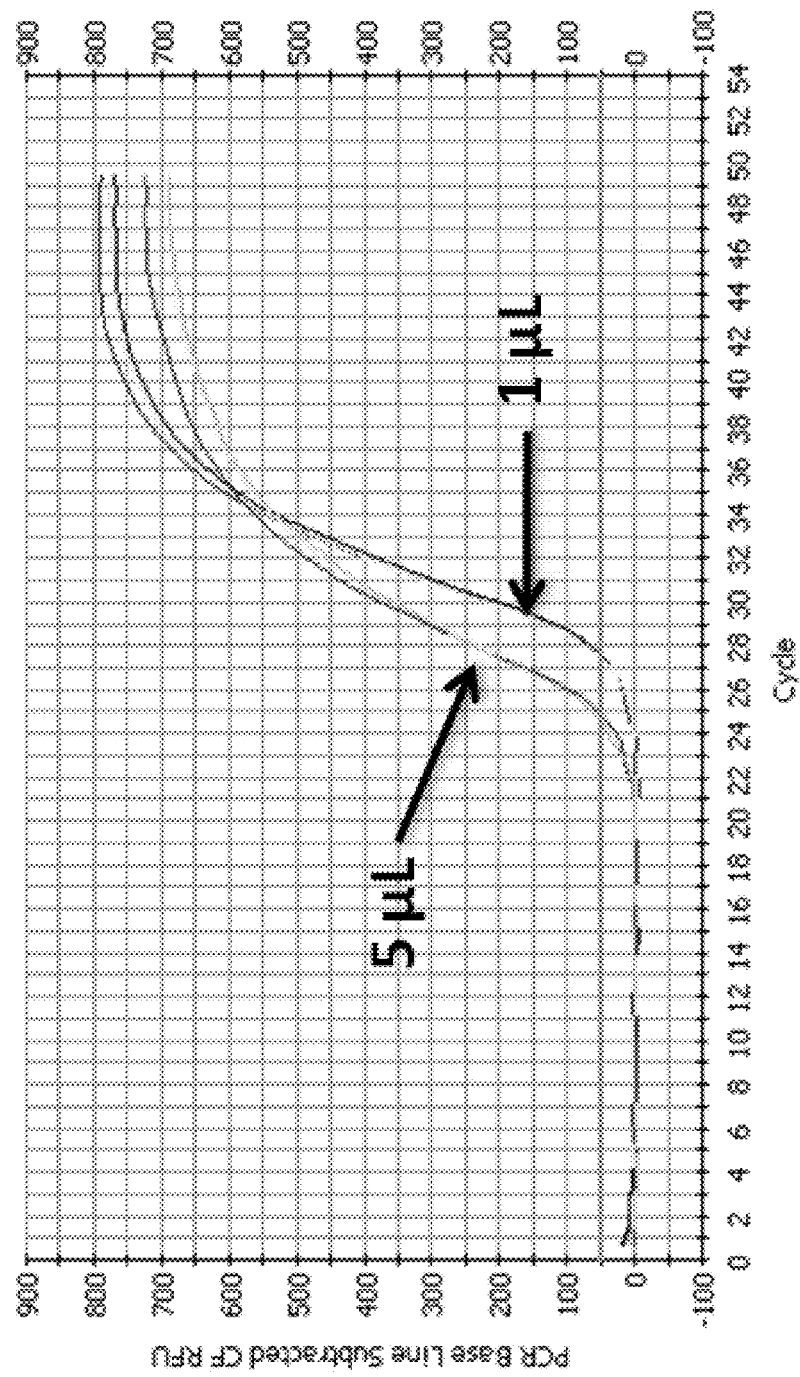
Figure 10D:
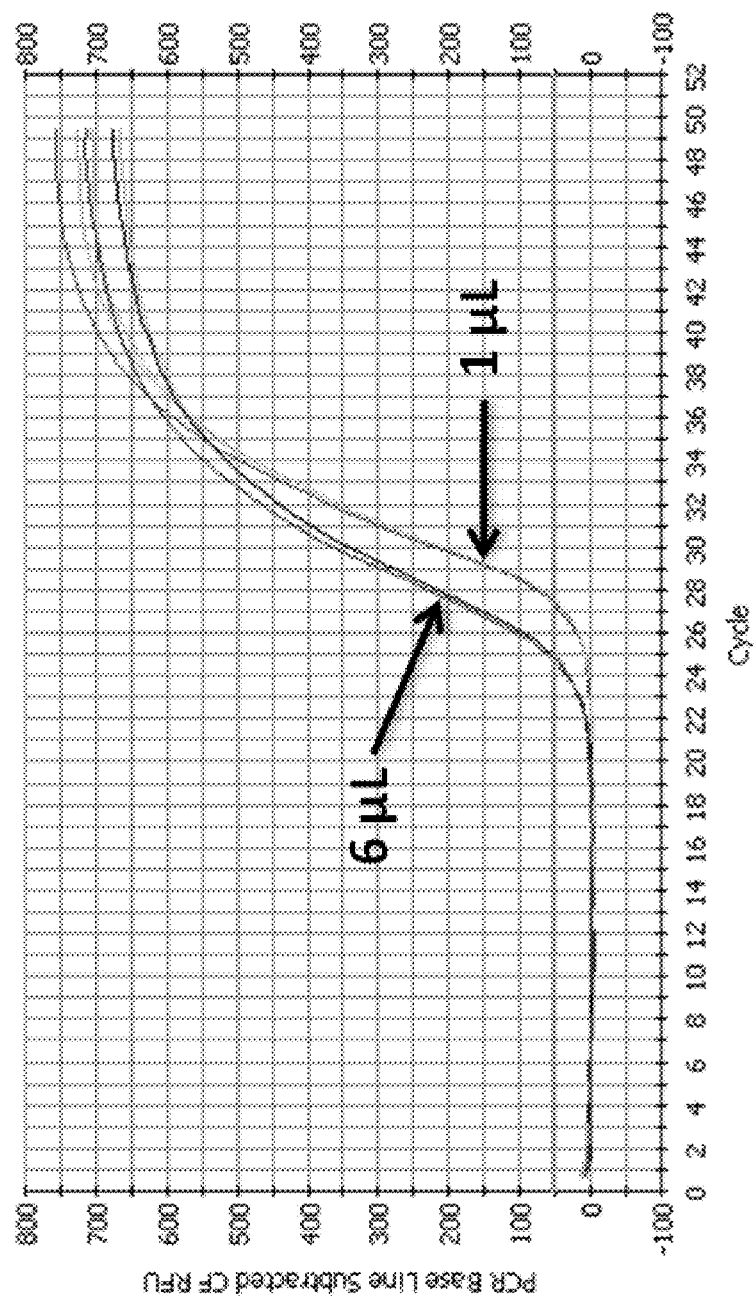

Next, spin column filtration was tried as an alternative method to separate the PVP from the stool supernatant. The smaller particle size PVP could not be processed in this manner as the PVP apparently packed down so tightly in the spin column that the liquid stool supernatant could not pass through. However, the larger particle size PVP did not have this same problem and the sample preparation could easily be spin filtered. The spin column contained a polyethylene frit (20-micrometer nominal pore size) to collect the PVP. When separating the large particle PVP from the stool supernatant via spin column filtration equipped with a polyethylene frit, the eluate volume in the qPCR could be increased to 5 microliters or 6 microliters without obvious inhibition (see FIGS. 10C and 10D). As shown in Table 1, when using 5 or 6 microliters of eluate, the calculated strand number was approximately five or six times the calculated strand number when using 1 microliter of eluate. These results demonstrate the benefits of PVP treatment plus spin column filtration for removal of PCR inhibitors from stool samples.

TABLE 1

| Treatment | Volume | Strands | % Expected |
|---|---|---|---|
| PVPP 30-50 | 1 µL | 950 | |
| No spin filter | 5 µL | no signal (complete inhibition) | 0 |
| PVPP 100-130 | 1 µL | 907 | |
| No spin filter | 5 µL | no signal (complete inhibition) | 0 |
| PVPP 100-130 With spin filter | 1 µL 5 µL | 1136 6751 | 119 |
| PVPP 100-130 With spin filter | 1 µL 6 µL | 3110 18600 | 99.68 |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method for amplifying a target nucleic acid from a crude human stool sample preparation comprising a nucleic acid, the method comprising:
   a) mixing insoluble cross-linked polyvinylpyrrolidone particles in powder, granule, or tablet form with said crude human stool sample preparation in an amount of 50 milligrams of insoluble cross-linked polyvinylpyrrolidone particles per milliliter of crude sample preparation, under conditions wherein said assay inhibitor binds to said polyvinylpyrrolidone particles to produce an insoluble complex in a suspension;
   b) separating said insoluble complex from said suspension, wherein said separating comprises filtering said suspension through porous filtering material, wherein during said filtering said insoluble complex is retained by said porous filtering material, and wherein a liquid fraction of said suspension passes through porous filtering material to produce a clarified sample preparation comprising said nucleic acid;
   c) capturing target nucleic acid from said clarified sample preparation and eluting captured target nucleic acid to form an eluted nucleic acid solution; and d) conducting a polymerase chain reaction in a reaction volume, wherein at least $\frac{1}{5}^{th}$ of the reaction volume of said polymerase chain reaction is eluted nucleic acid solution of c).

2. The method of claim 1 wherein said crude human stool sample preparation is a supernatant prepared from a human stool sample.

3. The method of claim 1, wherein said porous filtering material is in a spin filter, and wherein said filtering comprises centrifuging.

4. The method of claim 1, wherein said insoluble crosslinked polyvinylpyrrolidone particles comprise particles having a diameter between 100 and 130 micrometers.

5. The method of claim 1, wherein said porous filtering material comprises pores of less than 45 micrometers.

6. The method of claim 3, wherein said spin filter comprises a porous frit.

7. The method of claim 1,
wherein said target nucleic acid is human DNA.

8. The method of claim 7, wherein said human DNA is indicative of colon cancer and/or adenoma.

\* \* \* \* \*